United States Patent [19]

Wiles

[11] Patent Number: Plant 6,637

[45] Date of Patent: Feb. 28, 1989

[54] ACHIMENES PLANT NAMED PICOTEE ROSE

[75] Inventor: Linda S. Wiles, Greenwood, S.C.

[73] Assignee: Geo. W. Park Seed Co., Inc., Greenwood, S.C.

[21] Appl. No.: 103,035

[22] Filed: Sep. 30, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A cultivar of Achimenes plant named Picotee Rose.

2 Drawing Sheets

The present invention comprises a new and distinct cultivar of Achimenes plant, hereinafter referred to by the cultivar name Picotee Rose.

Picotee Rose is a product of a planned breeding program which had the objective of creating new Achimenes cultivars having superior vigor, good branching habits, suitability for pot plants or hanging baskets, double flowers 2" or more in diameter and of various colors, early-flowering, floriferousness, and a long flowering season. Such traits in combination were not present or needed improvement in previously available commercial cultivars of this type.

Picotee Rose was originated from a hybridization made in a controlled breeding program in Greenwood, S.C. in 1984. Both the male and female parent were identified by the breeding number 840942-2, with the female parent being selfed from the male parent.

Picotee Rose was discovered and selected as one flowering plant within the progeny of the stated parentage by Linda Saussy Wiles on Aug. 21, 1985, in a controlled greenhouse environment in Greenwood, S.C.

Asexual reproduction of the new cultivar by rhizomes, as performed initially by Linda Saussy Wiles at Greenwood, S.C. has demonstrated that the combination of characteristics as herein disclosed for Picotee Rose are firmly fixed through successive generations of asexual reproduction.

Picotee Rose has not been observed under all possible environmental conditions. The phenotype may vary significantly with variations in environment such as temperature, light intensity, and day length. The following observations, measurements, and comparisons describe plants grown in Greenwood, S.C. under greenhouse conditions which approximate those generally used in commercial practice.

The following traits have been repeatedly observed and are determined to be basic characteristics of Picotee Rose, which in combination distinguish this Achimenes as a new and distinct cultivar:

(1) The flowers are double in form and large, being 2⅛" to 2 11/16" diameter. There are five (5) full size petals and 5 or more smaller petals measuring 10/16"×10/16" or more when fully expanded.

(2) The upper surface flower color of the outer petals is an attractive white with a thin picotee or edge of light lavender to violet blue, with petals showing Silver White on the reverse or underside. If double petals are pulled apart the throat shows Light Chartreuse Green HCC 663/3, with some lines and dots of HCC 931/1×834/1 Dahlia Purple×Royal Purple also being apparent.

(3) Generally, two (sometimes one) flowers appear at each node. Plants are erect when young, and semi-trailing towards end of growing season.

(4) Rhizomes start growing early, producing plants rapidly. From rhizomes planted in early April, flowering plants were available by mid June.

(5) Plants continue to flower well into late November.

(6) Highly floriferous flowering habit.

Of the many commercial cultivars known to the present inventor, the most similar in comparison to Picotee Rose is Blue Rose, disclosed in U.S. Plant Pat. No. 5,919. Reference is made to attached Chart A which compares certain characteristics of Picotee Rose to those same characteristics of Blue Rose.

Picotee Rose can also be compared to White Rose, a cultivar of applicant disclosed in a pending application. Picotee Rose differs from White Rose by its larger flowers, lavender to blue picotee, and a slightly less floriferous habit. In addition, White Rose shows a pink tint near the center.

The accompanying color photographic drawings show typical inflorescence and foliage characteristics of Picotee Rose, with the colors being as nearly true as possible with illustrations of this type. Sheet 1 is a perspective view of the plant, and sheet 2 comprises a greatly enlarged photo of a single flower and surrounding foliage.

In the following description, color references are made to the Horticultural Color Chart (HCC), or to The Royal Horticultural Society Colour Chart (R.H.S.) where indicated. The color values were determined between 3:00 pm. and 4:00 pm. on Sept. 23, 1986 under 2100 foot candles of light intensity at Greenwood, S.C.

Classification:

A. *Botanical.*—Achimenes hybrid., cv. Picotee Rose.

B. *Commercial.*—Achimenes.

PLANT

A. General appearance:

*Height.*—Erect when young; semi-trailing later.

*Growth.*—Bushy.

*Internode.*—Distance 1"-1.5" (2.5 cm to 3.8 cm).

B. Foliage:

*Leaves.*—Numerous.

*Shape.*—1/16″×1½″ to 1⅜″×2″. (2.7 cm by 3.8 cm to 3.5 cm by 5.1 cm).

*Appearance.*—Serrated.

*Color.*—Top side Parsley Green HCC 0962. Bottom side Pod Green-Parsley Green. HCC 061/3×0962/3.

*Texture.*—Pubescent on both upper and lower surfaces.

C. Flowers:

*Borne:* 2 flowers per node at most nodes.

*Type of stems:* Short.

*Number of flowers per stem:* One.

*Quantity of blooms:* Abundant.

D. Blooms:

*Size.*—2⅛″ to 2 11/16″ (5.4 cm to 6.8 cm).

*Petalage.*—Double, five (5) full size outer petals, 5 or more smaller inner petals.

*Shape.*—Approximately round.

*Color.*—Outside petals, upper surface White with a thin picotee Pastel Lavender HCC 440 to Hyacinth Blue HCC 40/2 in color; under surface Silver White. Inner petals, upper surface White with a thin picotee Pastel Lavender HCC 440 to Hyacinth Blue HCC 40/2; sometimes young petals with very light tint of Pastel Lavender HCC 440 to White. If inner petals are pulled apart then HCC 663/3 Chartreuse Green is partially visible with Purple HCC 931/1×834/1 lines, and dots being apparent.

E. Reproductive organs:

*Stamens.*—0–5, usually staminode.

*Filaments.*—0–5, usually attached to petals.

*Anthers.*—0.

*Pollen.*—None.

*Pistils.*—1, deformed.

*Styles.*—1, very reduced and deformed, or about ½ length of flowers flattened laterally.

*Seed.*—Will not normally produce seed.

Disease Resistance: No known disease problems on plants.

CHART A

| CHARACTERISTIC | BLUE ROSE | PICOTEE ROSE |
|---|---|---|
| Flower size | 1.7″–2.0″ | 2.1″–2.7″ |
| Smaller petals | 4–6, 0.6″ × 0.6″ | 5, 0.6″ × 0.6″ |
| Leaf size | 1.0″ × 1.7″–2.5″ | 1.1″ × 1.5″ to 1.4″ × 2.0″ |
| Leaf color | HCC 0962 Parsley Green; HCC 061/3 Pod Green reverse | HCC 0962 Parsley Green; HCC 061/3 × 0962/3 Pod Green-Parsley Green reverse |
| Internode spacing | 0.7″–1.2″ | 1.0″–1.5″ |
| Flowers per node | 2–3 | usually 2 (sometimes 1) |
| Stamens | 0–4 | 0–5, usually staminode |
| Filaments | 4, sometimes attached to petals | 0–5, usually attached to petals |
| Anthers | variable, 0–4 | 0 |
| Pollen | some on occasion | none |
| Pistils | 1 | 1, deformed |
| Styles | 1, normal | 1, very reduced and deformed, or about ½ length of flower and flattened laterally |
| Flower color | HHC 40/2 Hyacinth Blue, with Silver White reverse; if petals retract, HCC 601/3 Primrose Yellow and HCC 28 Fuschia Purple lines and dots are visible in throat | White with thin picotee of Light Lavender to Violet Blue, with Silver White reverse; HCC 663/3 Light Chartreuse Green and HCC 931/1 × 834-1 Dahlia Purple × Royal Purple |

I claim:

1. A new and distinct cultivar of Achimenes plant named Picotee Rose, as illustrated and described.

* * * * *

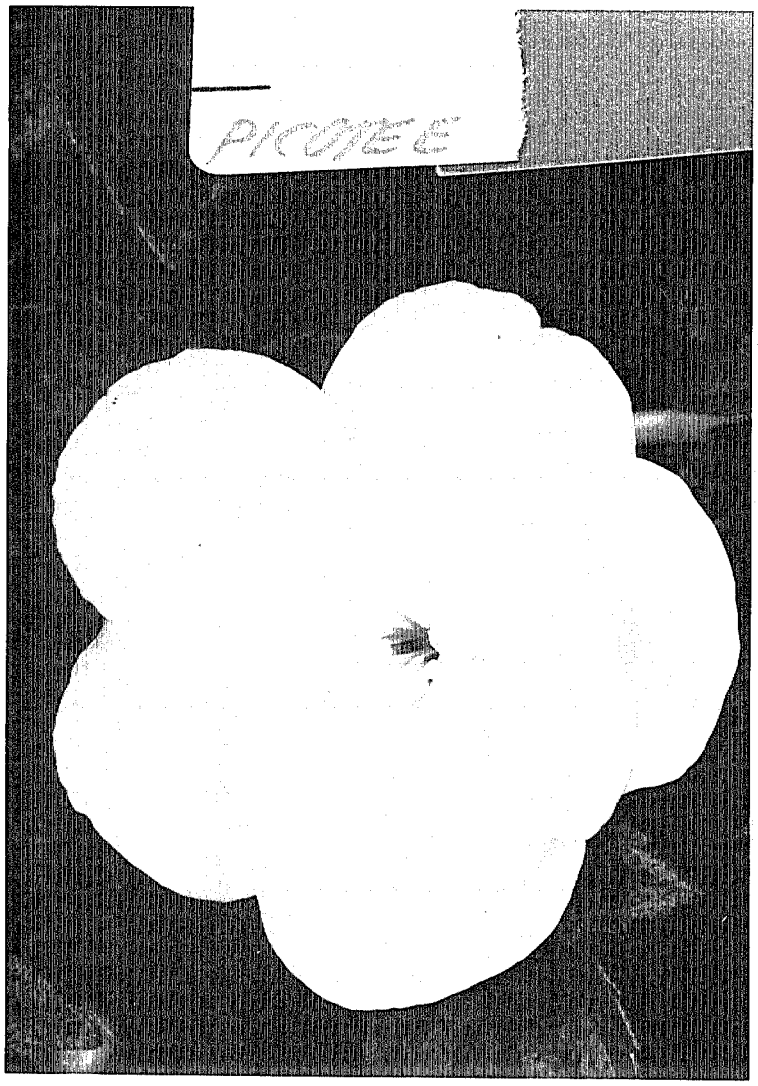
PROTEE

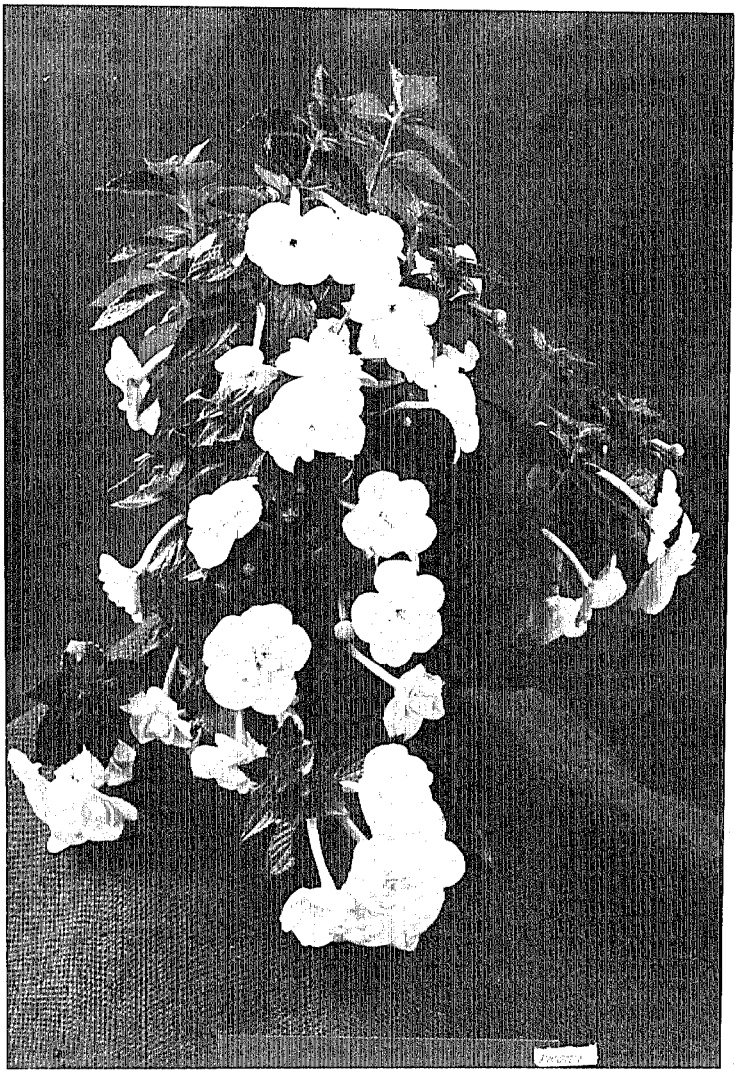

UNITED STATES PATENT AND TRADEMARK OFFICE

CERTIFICATE OF CORRECTION

PATENT NO. : Plant 6,637

DATED : February 28, 1989

INVENTOR(S) : Linda S. Wiles

It is certified that error appears in the above-identified patent and that said Letters Patent is hereby corrected as shown below:

In Column 2, lines 27-30, the final two sentences of the paragraph should read:

> Sheet 1 comprises a greatly enlarged photo of a single flower and surrounding foliage. Sheet 2 is a perspective view of the plant.

Signed and Sealed this

Thirteenth Day of February, 1990

*Attest:*

JEFFREY M. SAMUELS

*Attesting Officer*

*Acting Commissioner of Patents and Trademarks*